US008868185B2

(12) United States Patent
Zielinski et al.

(10) Patent No.: US 8,868,185 B2
(45) Date of Patent: Oct. 21, 2014

(54) USE OF THORACIC AND EXTRA-THORACIC IMPEDANCE FOR DIAGNOSTIC MONITORING

(71) Applicant: Medtronic, Inc., Minneapolis, MN (US)

(72) Inventors: Todd M. Zielinski, Ham Lake, MN (US); Douglas A. Hettrick, Maple Grove, MN (US); Yong K. Cho, Maple Grove, MN (US); Eduardo N. Warman, Maple Grove, MN (US); Paul A. Sobotka, West St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 29 days.

(21) Appl. No.: 13/686,359

(22) Filed: Nov. 27, 2012

(65) Prior Publication Data
US 2014/0148867 A1    May 29, 2014

Related U.S. Application Data

(60) Provisional application No. 61/553,524, filed on Oct. 31, 2011.

(51) Int. Cl.
*A61N 1/368* (2006.01)
*A61N 1/365* (2006.01)
*A61M 27/00* (2006.01)

(52) U.S. Cl.
CPC ........... *A61N 1/36507* (2013.01); *A61M 27/00* (2013.01)
USPC .................................................. 607/17; 607/7

(58) Field of Classification Search
USPC ....................................................... 607/17, 7
See application file for complete search history.

(56) References Cited

U.S. PATENT DOCUMENTS

| 5,305,745 A | 4/1994 | Zacouto |
| 5,501,702 A | 3/1996 | Plicchi |
| 5,902,325 A | 5/1999 | Condie |
| 6,044,297 A | 3/2000 | Sheldon |
| 6,073,048 A | 6/2000 | Kieval |
| 6,418,346 B1 | 7/2002 | Nelson |
| 6,442,433 B1 | 8/2002 | Linberg |
| 6,480,745 B2 | 11/2002 | Nelson |

(Continued)

FOREIGN PATENT DOCUMENTS

WO          9612440 A1    2/1996

OTHER PUBLICATIONS

Khoury DS, et al. "Ambulatory Monitoring of Congestive Heart Failure by Multiple Bioelectric Impedance Vectors", JACC, 2009, vol. 53(12).

(Continued)

*Primary Examiner* — Christopher D Koharski
*Assistant Examiner* — Michael Carey
(74) *Attorney, Agent, or Firm* — Michael C. Soldner

(57) ABSTRACT

A medical device and associated method for delivery of a cardiac therapy that includes determining a first impedance signal along a thoracic electrode vector extending within a portion of a thoracic cavity, determining a second impedance signal along an extra-thoracic electrode vector extending outside the thoracic cavity, comparing first amplitude measurements corresponding to the first impedance signals and second amplitude measurements corresponding to the second impedance signals, comparing first slope measurements corresponding to the first impedance signals and second slope measurements corresponding to the second impedance signals, and determining delivery of the cardiac therapy in response to the comparing.

12 Claims, 7 Drawing Sheets

(56) References Cited

U.S. PATENT DOCUMENTS

| | | |
|---|---|---|
| 6,599,250 B2 | 7/2003 | Webb |
| 7,096,064 B2 | 8/2006 | Deno |
| 7,672,718 B2 | 3/2010 | Stahmann |
| 7,769,451 B2 | 8/2010 | Yang |
| 7,899,526 B2 | 3/2011 | Benditt |
| 2005/0080460 A1 | 4/2005 | Wang |
| 2006/0287600 A1 | 12/2006 | Mceowen |
| 2007/0270707 A1 | 11/2007 | Belalcazar |
| 2008/0249583 A1* | 10/2008 | Salo et al. ............ 607/11 |
| 2008/0262361 A1 | 10/2008 | Gutfinger |
| 2009/0012416 A1 | 1/2009 | Belalcazar |
| 2009/0036777 A1 | 2/2009 | Zhang |
| 2009/0062730 A1 | 3/2009 | Woo |
| 2009/0069708 A1 | 3/2009 | Hattlestad |
| 2009/0198302 A1 | 8/2009 | Anderson |
| 2009/0275854 A1 | 11/2009 | Zielinski |
| 2009/0276025 A1 | 11/2009 | Burnes |
| 2010/0004714 A1 | 1/2010 | Georgakopoulos |
| 2010/0113888 A1 | 5/2010 | Cho |
| 2010/0113890 A1 | 5/2010 | Cho |
| 2010/0114204 A1* | 5/2010 | Burnes et al. ............ 607/4 |
| 2011/0022127 A1 | 1/2011 | Averina |
| 2011/0190654 A1 | 8/2011 | Hettrick |

OTHER PUBLICATIONS

P0041250.WOU4 (PCT/US2012/066810) PCT Notification of Transmittal of the International Search Report and the Written Opinion of the International Searching Authority.

* cited by examiner

USE OF THORACIC AND EXTRA-THORACIC IMPEDANCE FOR DIAGNOSTIC MONITORING

CROSS-REFERENCE TO PRIORITY APPLICATION

The present application claims priority and other benefits from U.S. Provisional Patent Application Ser. No. 61/553,524, filed Nov. 29, 2011, incorporated herein by reference in its entirety.

CROSS-REFERENCE TO RELATED APPLICATION

Cross-reference is hereby made to the commonly-assigned related U.S. application Ser. No. 13/686,308, entitled "USE OF THORACIC AND EXTRA-THORACIC IMPEDANCE FOR DIAGNOSTIC MONITORING", to Zielinski, et al., filed concurrently herewith and incorporated herein by reference in it's entirety.

FIELD OF THE DISCLOSURE

The disclosure relates generally to medical devices and, in particular, to an apparatus and method for monitoring a patient using thoracic and extra-thoracic impedance measurements.

BACKGROUND

Thoracic impedance measurements have been proposed for use in monitoring pulmonary edema in heart failure patients. As fluid accumulates in the lungs secondary to heart failure, impedance measured in the thoracic cavity decreases. Early detection of pulmonary edema in heart failure patients enables early therapeutic intervention, potentially reducing hospitalization and more severe symptoms.

Renal failure may occur secondary to heart failure or independently of heart failure and may result in hypertension, pulmonary edema, and tissue fluid accumulation. Fluid status monitoring is therefore a potentially important clinical tool in managing patients that suffer from heart failure and/or renal failure. The overlapping causes and symptoms of pulmonary edema can pose a challenge in diagnosing and treating the patient condition. A need remains for a device and associated method for diagnostic monitoring of acute heart failure decompensation or other conditions associated with edema.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
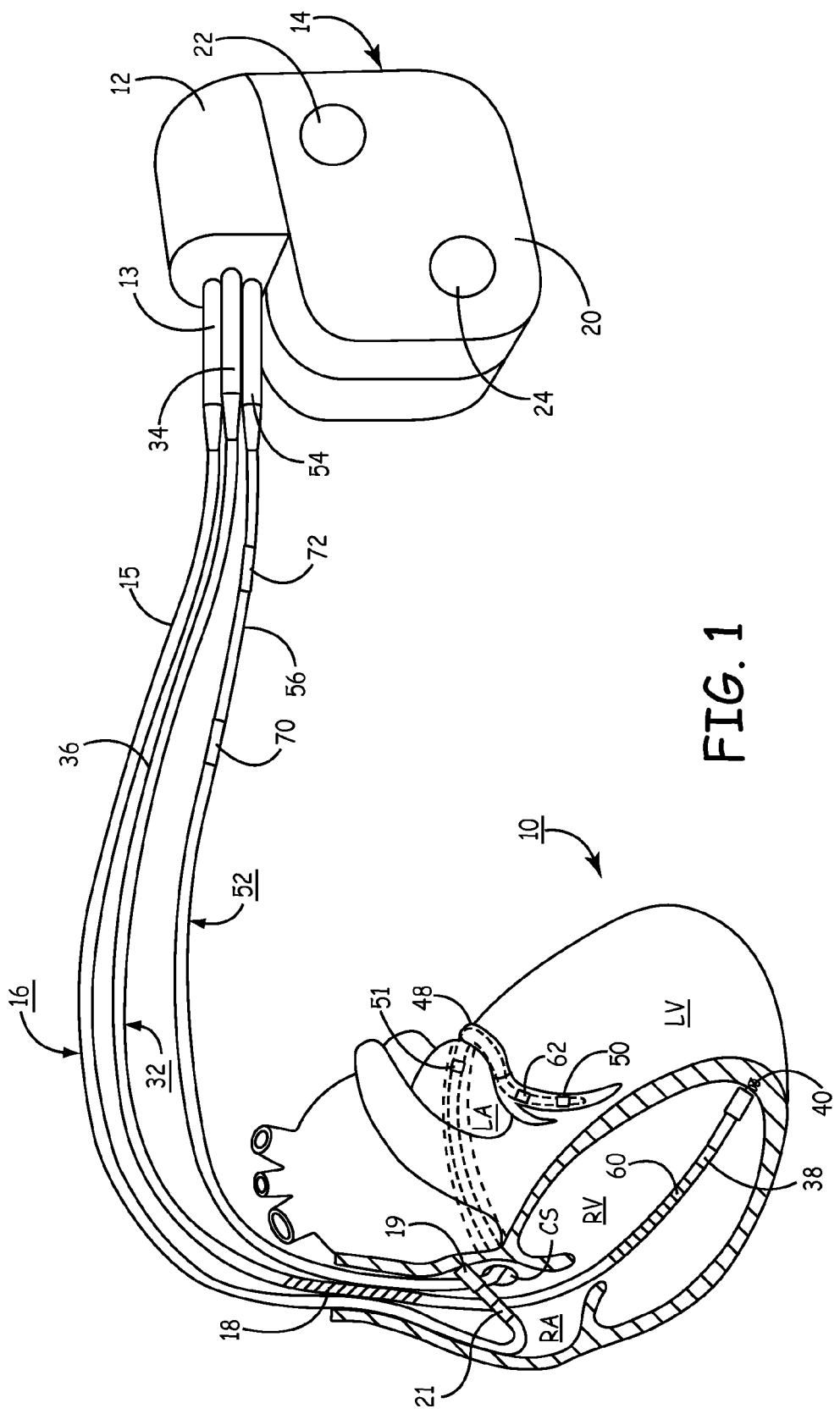
FIG. 1 depicts an implantable medical device (IMD) in which monitoring and therapy control methods described herein may be implemented.

FIG. 1 depicts an implantable medical device (IMD) 14 in which monitoring and therapy control methods described herein may be implemented. Various embodiments of the invention may be implemented in numerous types of implantable medical devices configured for measuring impedance signals, such as pacemakers, implantable pacemaker cardioverter defibrillators (ICDs), ECG monitors, and hemodynamic monitors. In the embodiment shown, IMD 14 is provided for sensing intrinsic heart activity and delivering cardiac stimulation pulses in the form of pacing, cardioversion or defibrillation therapy, as appropriate, to one or more heart chambers. IMD 14 may be configured to generate electrical signals for pacing the heart 10 or for delivering neurostimulation for treating heart failure and/or renal failure or conditions associated therewith. Such therapies may include cardiac resynchronization therapy, vagal nerve stimulation, baroreflex modulation, or other neural stimulation therapies. Other examples of devices and systems for delivering therapies for treating heart failure are generally disclosed in commonly-assigned U.S. Pat. No. 8,315,713 (Burnes et al.), U.S. Pat. No. 6,073,048 (Kieval et al.), and U.S. Pat. No. 7,769,451 (Yang et al.), all of which are hereby incorporated herein by reference in their entirety.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect IMD 14 with the RA, the RV and the LV, respectively. Each lead has at least one electrical conductor and pace/sense electrode. A remote indifferent can electrode is formed as part of the outer surface of the IMD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber. RA lead 16 is formed with a connector 13 fitting into a connector bore of IMD connector block 12 for electrically coupling RA tip electrode 19 and RA ring electrode 21 to IMD circuitry housed within housing 20 via insulated conductors extending within lead body 15. RA tip electrode 19 and RA ring electrode 21 may be used in a bipolar fashion, or in a unipolar fashion with IMD housing electrodes 22 or 24, for achieving RA stimulation and sensing of RA EGM signals.

RV lead 32 is passed through the RA into the RV where its distal end carries RV tip electrode 40 and RV ring electrode 38 provided for electrical stimulation in the RV and sensing of RV EGM signals. RV lead 32 optionally carries high-voltage coil electrodes 18 and 60 for use in cardioverting and defibrillating heart 10 in response to the detection of tachycardia or fibrillation. RV lead 32 is formed with a connector 34 fitting into a corresponding connector bore of IMD connector block 12. Connector 34 is coupled to electrically insulated conductors within lead body 36 and connected with distal tip electrode 40, ring electrode 38 and coil electrodes 18 and 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of IMD connector block 12 to provide electrical coupling of conductors extending from electrodes 50 and 62 within lead body 56 to IMD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

CS lead 52 is additionally shown to include an array of two or more subcutaneous electrodes 70 and 72 positioned at proximal locations along lead body 56 such that when CS lead 52 is advanced transvenously into a cardiac vein, electrodes 70 and 72 are positioned subcutaneously, outside the thoracic cavity. IMD 14 may further include one or more subcutaneous cardiac sensing electrodes 22 and 24 formed as uninsulated portions of the IMD housing 20 or included in the connector block 12. Electrodes 70 and 72 or electrodes 22 and 24 or any combination thereof may be used to obtain subcutaneous, extra-thoracic impedance signals in some embodiments.

Any of the electrodes carried by leads 16, 32 and 52 positioned within the thoracic cavity, in this case within or along heart 10, are used for obtaining a thoracic impedance signal. As will be further described herein, at least one thoracic impedance signal and at least one extra-thoracic impedance signal are acquired to determining a fluid status measurement for monitoring the patient. As used herein, a "fluid status measurement" is a measurement derived from both a thoracic impedance signal and an extra-thoracic impedance signal and is correlated to the amount of fluid present in the thoracic cavity and in tissue outside the thoracic cavity. The fluid status measurement may be used to track the accumulation of fluid as a condition worsens, such as congestive heart failure or renal failure, as well as the removal of fluid as a condition improves or in response to a therapy.

As used herein, a thoracic impedance signal includes any impedance signal obtained using a measurement electrode vector that encompasses or traverses at least a portion of the thoracic cavity, which may include portions of the lungs and/or heart 10 and great vessels. A thoracic impedance signal is not limited to signals obtained by electrodes located within the thorax. In some embodiments, impedance measuring electrodes may be positioned extra-thoracically such that an impedance measurement vector extends through a portion of the thorax to obtain a thoracic impedance signal.

As used herein, an extra-thoracic impedance signal includes any impedance signal that is obtained using a measurement vector that is substantially outside the thorax and substantially excludes the thoracic cavity, heart and lungs. The extra-thoracic impedance signal is generally a tissue impedance signal that may include submuscular, intra-abdominal, or other impedance measurement tissue volumes that are obtained to measure the impedance of a tissue volume that is outside the thoracic cavity. As such, an extra-thoracic impedance measurement vector could include an electrode positioned on an inner wall of the thoracic cavity paired with an electrode located outside the thoracic cavity such that the impedance measurement vector extends outward from the thoracic cavity and does not include any significant volume of the thoracic cavity.

It is further contemplated that one or more impedance measuring electrodes may be positioned externally, for example attached to the patient's skin. A transthoracic impedance measurement could be obtained using one or more electrodes positioned cutaneously along the thorax. An extra-thoracic impedance measurement could be measured using one or more cutaneous electrodes for obtaining a tissue impedance measurement outside the thorax.

While a particular IMD system with associated leads and electrodes is illustrated in FIG. 1, numerous implantable cardiac monitoring, pacemaker and IMD system configurations are possible, which may include one or more leads or electrodes deployed in intra-vascular, extra-vascular, intra-thoracic, extra-thoracic or cutaneous locations. The lead and electrode arrangements will depend on the particular patient monitoring and therapy management application and IMD system used.

IMD 14 is shown as a multi-chamber device capable of sensing and stimulation in three or all four heart chambers. It is understood that IMD 14 may be modified to operate as a single or dual chamber device. Furthermore, it is contemplated that the patient monitoring techniques disclosed herein may be employed in a monitoring-only device that does not include therapy delivery capabilities. In some embodiments, IMD 14 may collect diagnostic data and transmit the data to an external programmer or other external device or to another implantable device for diagnostic or therapy management purposes.

Figure 2:
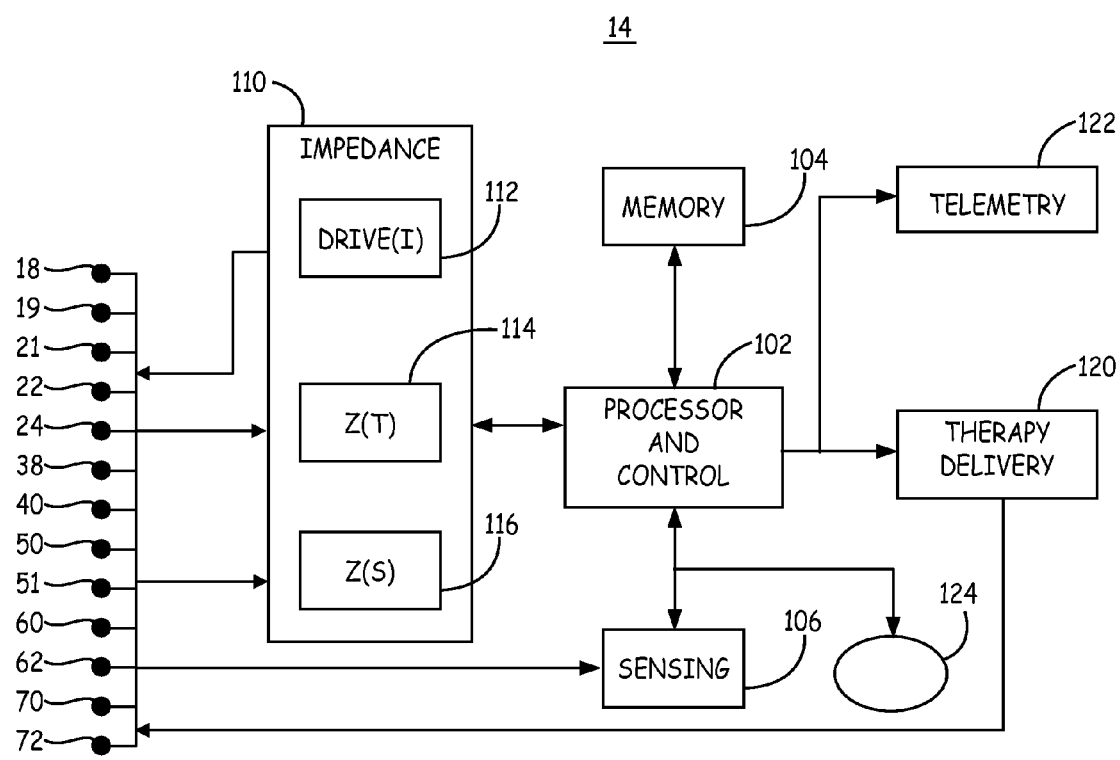
FIG. 2 is a functional block diagram illustrating one example configuration of IMD 14.

FIG. 2 is a functional block diagram illustrating one example configuration of IMD 14. IMD 14 includes a processor and control unit 102, memory 104, sensing module 106, therapy delivery module 120, and telemetry module 122. IMD 14 further includes impedance measurement module 110, which itself may include a drive signal generator 112 and measurement circuitry 114 and 116 for measuring a thoracic impedance signal, $Z(T)$, and an extra-thoracic impedance signal, $Z(S)$.

Memory 104 may include computer-readable instructions that, when executed by processor and control 102, cause IMD 14 to perform various functions attributed throughout this disclosure to IMD 10 and processor 102. The computer-readable instructions may be encoded within memory 104. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other non-transitory digital computer-readable media.

Processor and control unit 102 may include any one or more of a microprocessor, a controller, a digital signal processor (DSP), an application specific integrated circuit (ASIC), a field-programmable gate array (FPGA), or equivalent discrete or integrated logic circuitry. In some examples, processor 102 may include multiple components, such as any combination of one or more microprocessors, one or more controllers, one or more DSPs, one or more ASICs, or one or more FPGAs, as well as other discrete or integrated logic circuitry. The functions attributed to processor 102 herein may be embodied as software, firmware, hardware or any combination thereof.

Processor and control unit 102 includes a therapy control unit that controls therapy delivery module 120 to deliver a therapy according to a selected one or more therapy programs, which may be stored in memory 104. Therapy delivery module 120 may include a signal generator electrically coupled to electrodes 18, 19, 21, 38, 40, 50, 51, 60, 62, 70 and 71 (all of which are shown in FIG. 1), e.g., via conductors of the respective leads 16, 32 and 52, or, in the case of housing electrodes 22 and 24, via an electrical conductor disposed within housing 20 of IMD 14. Therapy delivery module 120 may be configured to generate and deliver electrical stimulation therapy to heart 20 via selected combinations of electrodes 18, 19, 21, 22, 24, 38, 40, 50, 51, 60, 62, 70 and 72. In some embodiments, therapy delivery module 120 is configured to deliver cardiac pacing pulses for delivering cardiac resynchronization therapy (CRT), neurostimulation pulses for delivering vagal nerve stimulation, or other types of electrical stimulation therapy.

Therapy delivery module 120 may include a switch module (not shown) and processor and control 102 may use the switch module to select, e.g., via a data/address bus, which of the available electrodes 18, 19, 21, 22, 24, 38, 40, 50, 51, 60, 62, 70 and 72 are used to deliver electrical stimulation pulses and coupled to signal generator included in therapy delivery module 120. The switch module may include a switch array, switch matrix, multiplexer, or any other type of switching device suitable to selectively couple a signal to selected electrodes.

In other embodiments, therapy delivery module 120 may include a fluid delivery pump for delivering a fluid to the patient, which may be a saline solution, pharmacological agent, or biological agent. When used to deliver a fluid, one of leads 16, 32, and 52 is modified to include a fluid delivery lumen or a separate fluid delivery catheter is coupled to therapy delivery module 120 to provide a fluid delivery path. Therapy delivery module 120 is optional and in some embodiments IMD 14 is provided as a monitoring device without therapy delivery capabilities.

Sensing module 106 may be provided for receiving cardiac electrical signals from any of electrodes 18, 19, 21, 22, 24, 38, 40, 50, 51, 60, 62, 70 and 72 in order to monitor electrical activity of heart 12. Sensing module 106 may also include a switch module to select which of the available electrodes are used to sense the cardiac activity. In some examples, processor 102 selects the electrodes to function as sense electrodes, or the sensing vector, via the switch module within sensing module 106.

In an example embodiment, sensing module 106 includes multiple detection channels, each of which may be selectively coupled to respective combinations of electrodes 18, 19, 21, 22, 24, 38, 40, 50, 51, 60, 62, 70 and 72 to detect electrical activity of a particular chamber of heart 10. Each detection channel may comprise an amplifier that outputs an indication to processor 80 in response to sensing of a cardiac depolarization, in the respective chamber of heart 10. In this manner, sensing module 106 may detect the occurrence of R-waves and P-waves in the various chambers of heart 10 and processor and control 102 may use sensed event signals received from sensing module 106 for controlling therapy delivery 120. Sensing module 106 may further include digital signal processing circuitry for providing processor 102 with digitized EGM signals as needed for performing EGM signal analysis.

Sensing module 106 may additionally or alternatively be coupled to other physiological sensors 124 for sensing signals useful in detecting a physiological condition of the patient. Sensors 124 may include, without limitation, an activity sensor, a posture sensor, a pressure sensor, an oxygen sensor, a temperature sensor or any combination thereof. Sensors 124 may be incorporated within or along the housing 20 of IMD 14 or be carried by a lead extending from IMD 14. In some embodiments, a wireless sensor may be positioned remotely from IMD 14 and telemetry module 122 may receive transmitted data from a remote sensor and provide the sensor signal data to processor and control 102.

Sensors 124 may provide signals to sensing module 106 or directly to processor and control 102 for use in controlling impedance measurement module 110 or for use in interpreting impedance signals. For example, impedance measurements may be acquired when the patient is known to be at rest, in a prone position, and in a standing or upright position so that positional changes on impedance signals can be examined.

Memory 104 stores algorithms, intervals, counters, or other data used by processor and control 102 to control IMD functions. In some embodiments, parameters stored in memory 104 are used to control the delivery of pacing pulses or other therapies delivered by therapy delivery module 120.

Telemetry module 122 provides communication with an external programmer or home monitor configured to communicate with IMD 14 via a wireless communication link. It is contemplated that IMD 14 may transmit to and receive programming data from an external programmer or home monitor that is coupled to a communications network for transferring data to a remote database or computer to allow remote management of a patient using the techniques described herein. Remote patient management systems may be configured to utilize the presently disclosed techniques to enable a clinician to review impedance signal data. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are incorporated herein by reference in their entirety.

A clinician may interact with a programmer (not shown) to transmit programming data to telemetry module 122 and to retrieve data from IMD 14 using an interrogation command. As such, an impedance monitoring protocol may be programmed into IMD 14 and acquired impedance-related data may be transmitted from IMD 14 to an external device using telemetry module 122. Telemetry module 122 may be controlled by processor and control 102 to generate an alert or notification signal to the patient or to a clinician that is transmitted from IMD 14 to an external device configured for wireless telemetry communication with telemetry module 122. Other types of patient alert signals may be generated by IMD 14 in response to detecting a patient condition based on impedance signals, such as audible sounds, a perceptible vibration or muscle stimulation.

Impedance measurement module 110 includes drive signal circuit 112 for generating a drive current signal applied to an excitation pair of electrodes selected from electrodes 18, 19, 21, 22, 24, 38, 40, 50, 51, 60, 62, 70 and 72. Impedance measurement circuitry 110 may include a switch module for selecting which electrodes are coupled to drive signal circuit 112 and impedance measurement circuits 114 and 116. Measurement circuits 114 and 116 are each coupled to respective recording electrode pairs selected from electrodes 18, 19, 21, 22, 24, 38, 40, 50, 51, 60, 62, 70 and 72 for recording a thoracic impedance signal and a extra-thoracic impedance signal.

A drive current signal may be applied to one or more excitation electrode pairs and the resulting thoracic impedance and extra-thoracic impedance may be recorded simultaneously. Impedance signals may be sampled at multiple time points over predetermined intervals of time to obtain a time-varying signal representing the fluid status of the patient and the influence of circadian variation, posture changes, therapy, or other interventions or perturbations on the impedance signals. As described above, a recording electrode pair that results in a measurement vector field residing substantially or entirely within the thoracic cavity is selected from electrodes 18, 19, 21, 22, 24, 38, 40, 50, 51, 60, 62, 70 and 72 for measuring a thoracic impedance. An extra-thoracic impedance recording electrode pair is selected from the available electrodes, such as electrodes 22, 24, 70 and 72, to establish a measurement vector field that resides substantially or entirely outside of the thoracic cavity for measuring extra-thoracic impedance.

Figure 3:
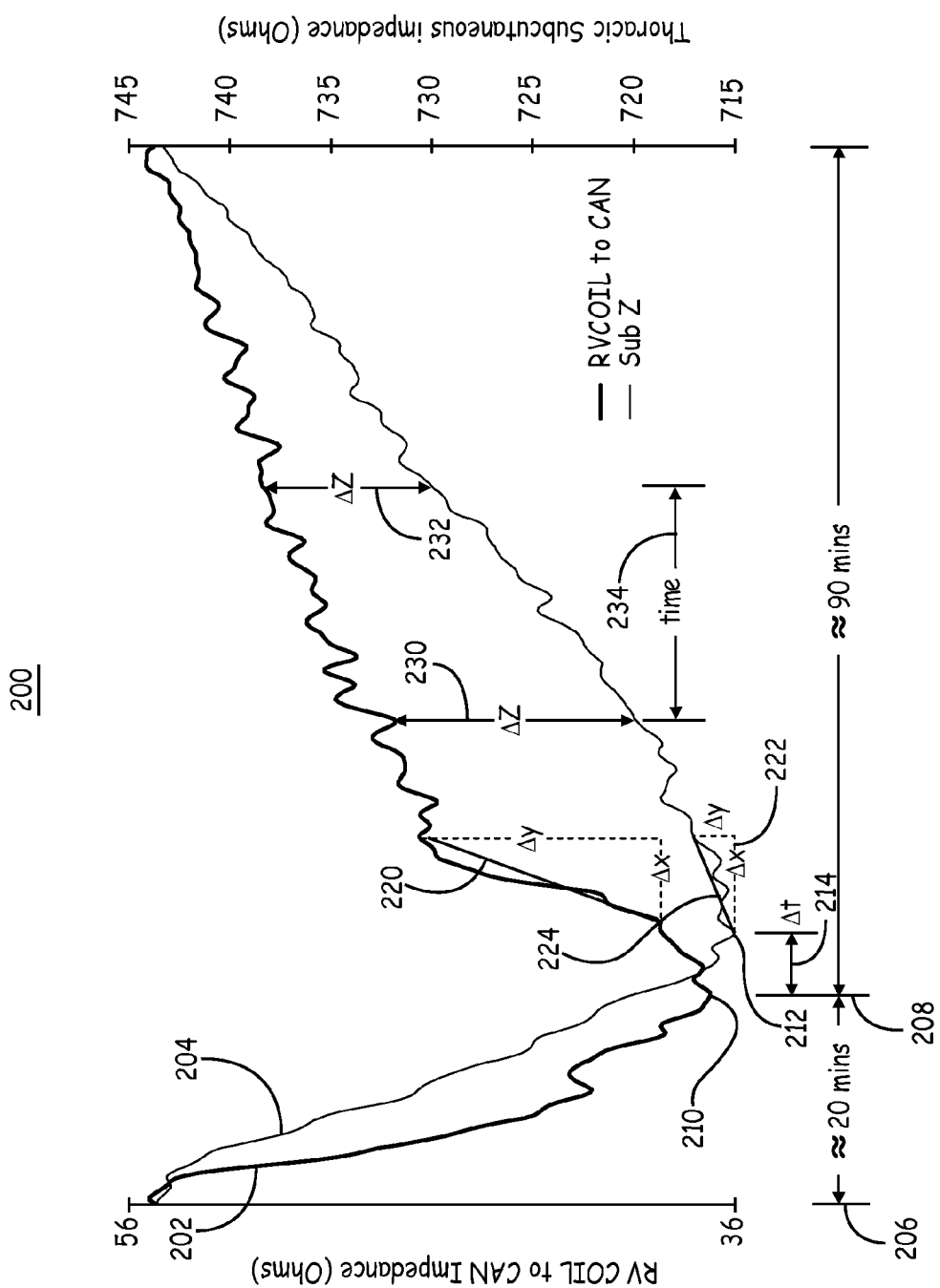
FIG. 3 is a plot of thoracic and extra-thoracic impedance signals acquired over time.

FIG. 3 is a plot 200 of thoracic and extra-thoracic impedance signals acquired over time. The thoracic impedance signal 202 is a mean impedance signal acquired from an RV lead using the RV coil electrode to IMD housing electrode as a recording electrode pair, e.g. RV coil 60 to IMD housing electrode 24. The extra-thoracic impedance signal 204 is a mean impedance signal acquired between a measurement pair of electrodes carried by a 4F lead implanted in a subject's right lateral thoracic subcutaneous space. In this example, the thoracic impedance signal corresponds to an intra-cardiovascular impedance measurement and the extra-thoracic impedance signal corresponds to an extra-cardiovascular impedance measurement.

The drive current signals for measuring the thoracic and extra-thoracic impedance signals 202 and 204 may be delivered using the same electrode pair as the recording pair (bipolar measurements), a common electrode with the respective recording electrode pairs and a separate electrode (tripolar measurements) or a different electrode pair than the recording pair (quadripolar measurements).

At a starting time 206, saline infusion is initiated and corresponding declines in both the thoracic impedance 202 and the extra-thoracic impedance 204 are observed. After an interval of acute volume overload by intravenous saline infusion, the pharmacologic diuretic agent Lasix (furosemide) was administered, beginning approximately at time 208, and subsequent thoracic and extra-thoracic volume depletion is observed as a rise in both impedance signals 202 and 204 after reaching respective minimum impedance values 210 and 212.

The extra-thoracic impedance minimum amplitude 212 lags the thoracic impedance minimum amplitude 210 by a time delay 214 of approximately eight minutes. A slope 220 measured from the thoracic impedance signal over a time interval 222 subsequent to the extra-thoracic impedance signal minimum 212 and a slope 224 measured from the extra-thoracic impedance signal over the same time interval 222 are determined to be significantly different. Likewise, the ratio of the slope 220 to the slope 224 changes notably over the time interval 236 of acute diuresis. Additionally, differences 230 and 232 in impedance signal amplitudes measured at periodic time intervals 234 after the onset of furosemide injection at time 208 are seen to decrease.

As will be further described below, a fluid status measurement is determined for a patient by recording both a thoracic impedance signal and an extra-thoracic impedance signal and using measurements obtained for both signals to compute the fluid status measurement. For example, a ratio, difference, difference in normalized impedance values or other amplitude-based measurements of the relative differences between the thoracic impedance signal and the extra-thoracic signal may be used in determining a fluid status measurement. Additionally or alternatively, a fluid status measurement may be determined using a time-based measurement derived from the thoracic and extra-thoracic impedance signals 202 and 204. A time-based measurement may be determined as a time interval between analogous fiducial points along the impedance signals 202 and 204, such as the time delay 214 between minimum impedance amplitudes 210 and 212. Alternatively, a time-based measurement may be determined as differences in time intervals between impedance signal fiducial points and a selected reference point, such as the onset of a detected change in patient position or other sensed physiological signal, time of day, onset, offset or adjustment of a therapy or other intervention.

In some embodiments, computing a fluid status measurement may include determining a slope measurement of each of the thoracic and extra-thoracic impedance signals 202 and 204, such as the slope measurements 220 and 224 determined over the same time interval 222 or other slopes defined by amplitude measurements obtained from the recorded impedance signals 202 and 204 over selected time intervals. Slope measurements that may be used for computing a fluid status measurement may be determined over different time intervals or the same time interval. In some embodiments, a slope measurement may be a maximum or minimum slope for each of the impedance signals 202 and 204 occurring during a monitoring interval, which may not occur simultaneously. Slope measurements of the impedance signals 202 and 204 may be determined at regular time intervals to determine a trend in the ratio of the impedance signal slopes over time.

A fluid status measurement may be computed using any of the above described measurements of the thoracic and extra-thoracic impedance signals or combinations thereof. The fluid status measurement is used for detecting a change in a heart failure or renal condition, which may cause an alert to be generated to notify the patient or a clinician of the condition. The fluid status measurement may be used in controlling a therapy delivered automatically by the IMD recording the impedance signals or by another device receiving fluid status measurement data. The fluid status measurement may be used for controlling the onset and end of a therapy as well as dosages or levels of therapy and therapy type. A fluid status measurement that includes a time interval measured between a thoracic and extra-thoracic impedance signal may indicate what therapy regimen should be used. For example, if the extra-thoracic signal lags the thoracic signal, a low dose diuretic with a vasodilator therapy may be indicated rather than a high dose diuretic therapy alone.

Figure 4:
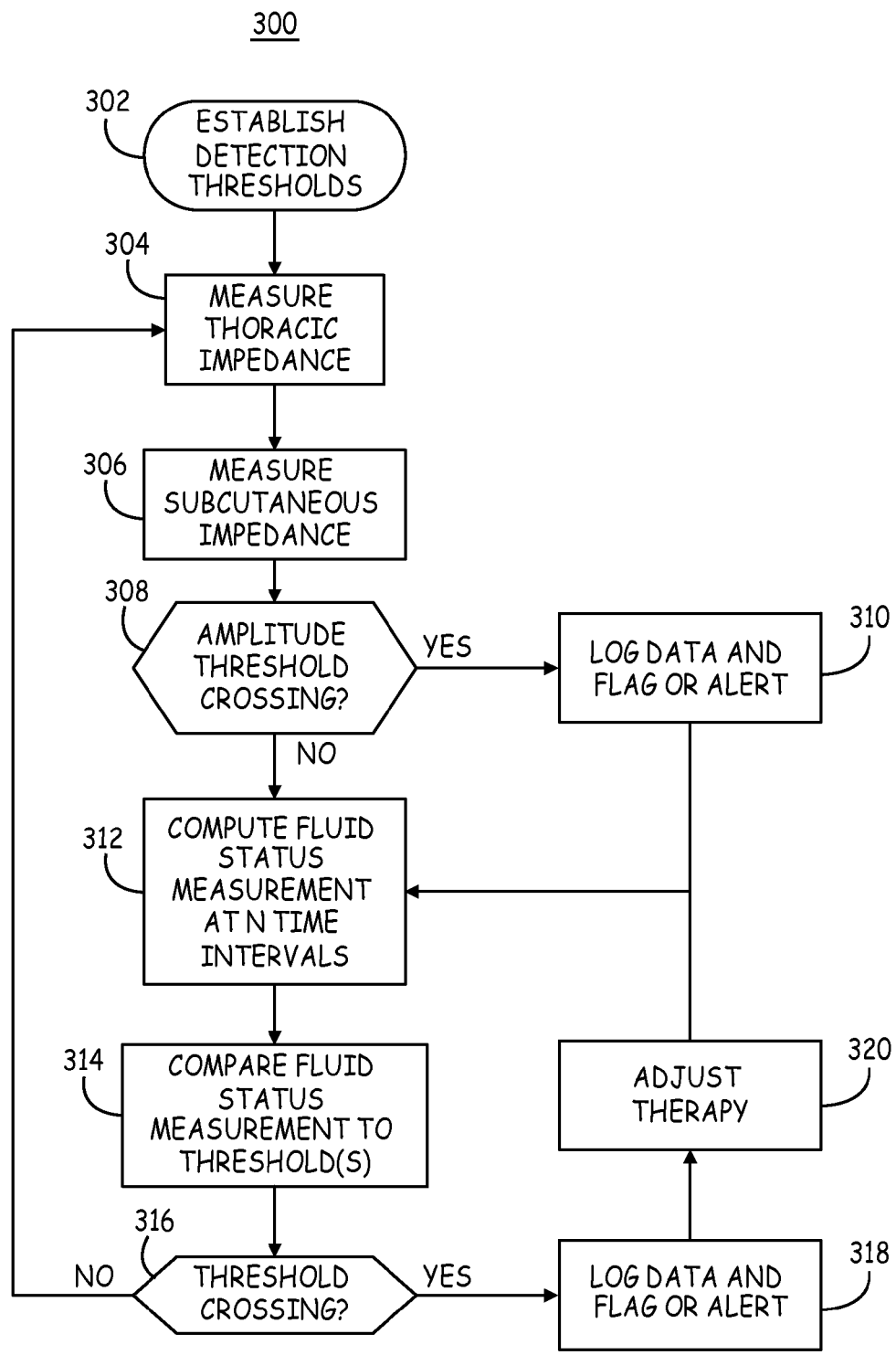
FIG. 4 is a flow chart of one method for monitoring a patient using impedance signals according to one embodiment.

FIG. 4 is a flow chart 300 of one method for monitoring a patient using impedance signals according to one embodiment. Flow chart 300 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a non-transitory computer-readable medium that includes instructions for causing a programmable processor to carry out the methods described. A "non-transitory computer-readable medium" includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 302, threshold criteria for detecting a patient condition relating to fluid status are established. Thresholds may be defined based on clinical data or based on baseline impedance measurements determined for the individual patient. The threshold criteria may be defined for detecting one or more fluid states relating to edema or fluid accumulation and/or hypovolemia or fluid loss and may define levels of a fluid status measurement determined from impedance signals at which clinician or patient alerts are generated or a therapy is adjusted or both.

At block 304, a thoracic impedance signal is measured. At block 306, an extra-thoracic impedance signal is measured. The impedance signals may be measured on a scheduled periodic basis, upon initiating a therapy or adjusting a therapy, or triggered upon other physiological signal input, such as a posture or activity change or a pressure measurement.

One or both impedance signals may compared to amplitude thresholds at block 308 to detect a low thoracic impedance or a low extra-thoracic impedance corresponding to fluid accumulation. If either impedance signal crosses a threshold, the impedance measurement may be logged and flagged in IMD memory at block 310. An alert may be generated to notify the patient and/or clinician directly or remotely via telemetry of the low impedance measurement. In some cases the threshold crossing detected at block 308 may be a high impedance threshold indicating potential hypovolumia secondary to over-diuresis.

A fluid status measurement is computed at block 312. The fluid status measurement is determined using both the thoracic impedance measurement and the extra-thoracic impedance measurement. Impedance signal amplitudes, slopes, time differences between fiducial points of the thoracic and extra-thoracic signals, or any combination thereof may be used to compute a fluid status measurement that combines features of both the thoracic and the extra-thoracic impedance measurements. Fluid status measurements can be used to identify a potential increase in cardiac congestion and to determine whether that increase is secondary to a global increase in total body fluid, or to a shift in fluid from another tissue compartment to the thoracic cavity. The differentiation between congestion due to fluid shift vs. fluid gain is clinically important since it could lead to different device or clinician-prescribed therapy regimes.

At block 314, the fluid status measurement is compared to a threshold and when a threshold crossing is detected (block 316), the impedance data and/or fluid status measurement may be logged in IMD memory at block 318. An alert signal may be generated to notify the clinician or patient of a change in fluid status that warrants attention. If the fluid status measurement does not cross a threshold, the impedance signals continue to be monitored at blocks 304 and 306 according to a programmed monitoring protocol.

At block 320, a threshold crossing may cause an adjustment to a therapy by the control processor of the IMD monitoring impedance or another IMD receiving fluid status measurement data. The adjustment to a pharmaceutical or other clinically administered therapy may be made manually in response to the data or an alert transmitted by the IMD to an external device. An adjustment may include determining the appropriate time to stop delivery of a therapy or reducing the dosage or the level or frequency of a given therapy.

The use of the fluid status measurement data may be combined with other clinical measurements in managing therapy. For example, a clinician may discontinue a diuretic therapy in response to increases in blood-derived bio-markers of worsening renal function (e.g. creatinine) indicating an apparent decreased blood volume. However, such blood markers do not consider potential excess fluid still residing in the tissue that has not had sufficient time to equilibrate with the circulating blood volume. This scenario can result in under-diuresis if the diuresis is performed too quickly to allow the interstitial fluid to remain in balance with the circulating blood volume. However, if the blood markers indicate reduced blood volume, and the fluid status measurement indicates fluid retention, then the diuretic therapy could be slowed or only temporarily discontinued to allow time for the remaining extravascular fluid to equilibrate with the reduced circulating blood volume. Such a method could help to avoid inadvertent clinical undertreatment of congestion.

In another embodiment, the fluid status measurement is used to improve the specificity pulmonary edema detection as compared to monitoring systems using only a thoracic impedance signal. Decreases in thoracic impedance can be associated with events besides acute heart failure decompensation such as acute anemia, pericardial effusion (tamponade) or pulmonary effusion. If a fluid status measurement indicates a decrease in thoracic impedance without a concomitant decrease in extra-thoracic impedance (absent acute diuresis as described above), then the fluid status measurement change is likely to be associated with a non-congestion induced drop in intrathoracic impedance. Accordingly, an alert or therapy response would withhold an acute heart failure decompensation response.

Figure 5:
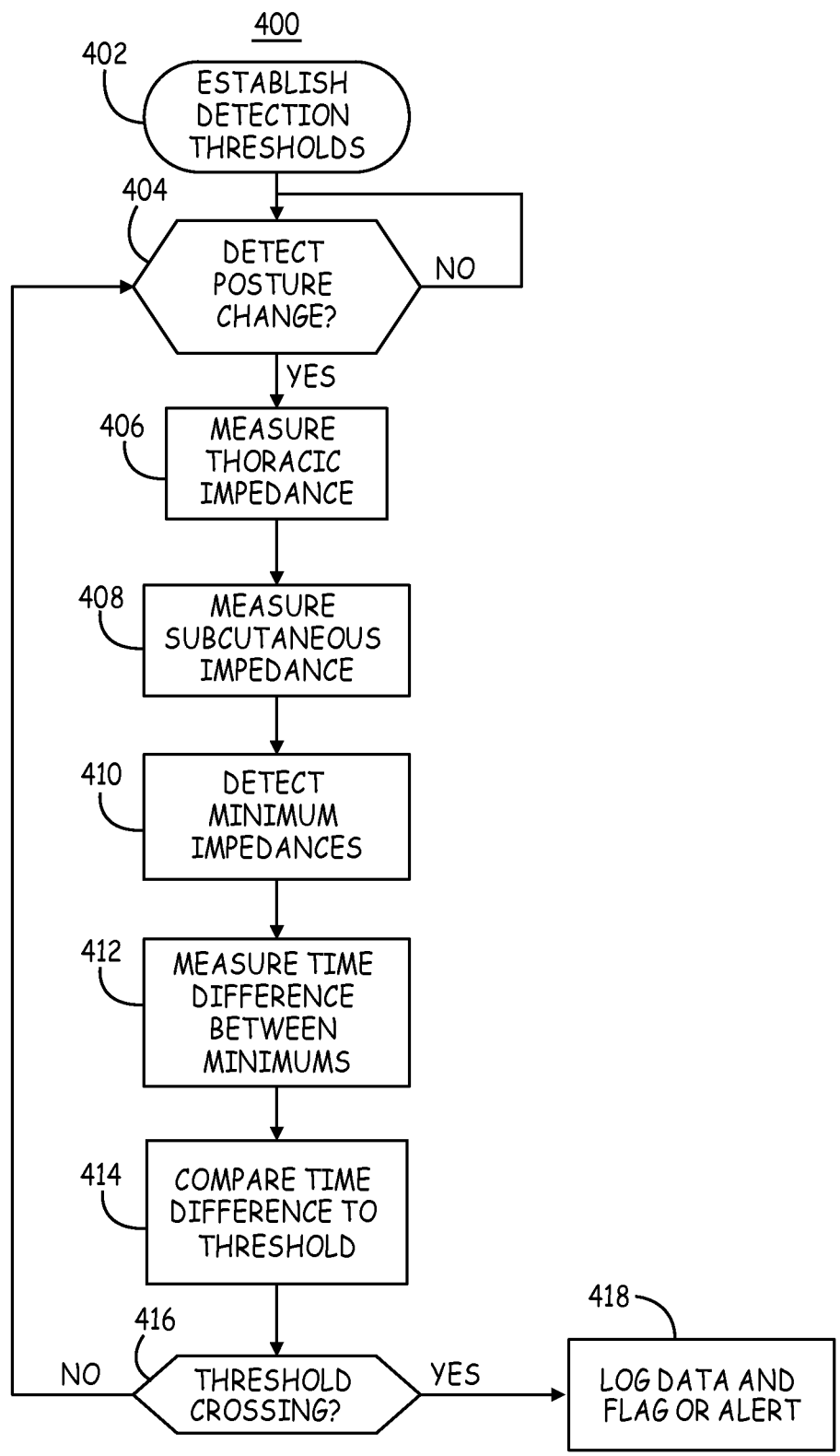
FIG. 5 is a flow chart of a method for monitoring the fluid status of a patient according to one embodiment.

FIG. 5 is a flow chart 400 a method for monitoring the fluid status of a patient according to one embodiment. At block 402, a fluid status measurement threshold is established. The threshold may be based on clinical data from a population of patients or based on individual baseline or other impedance measurements. At block 404, the patient's posture is monitored, e.g. using a combination of accelerometers as generally disclosed in commonly assigned U.S. Pat. No. 6,044,297 (Sheldon et al.), hereby incorporated herein by reference in its entirety. In one example, the posture may be monitored in combination with activity and/or time of day to detect when the patient is going to bed at night and/or when the patient rises. Impedance signal responses to the detected posture changes and diurnal or circadian rhythm can be used to determine a fluid status measurement or trends in the fluid status measurement taken at particular times of day may be examined over selected time periods.

In other embodiments, a different signal or triggering event may be detected or provided directly to initiate impedance signal recording, such as a heart rate change, activity change, or blood pressure change. An event used to initiate impedance signal monitoring may be an event that is expected to cause a perturbation in the fluid status of the patient, such as a posture change or heart rate change, that may cause a shift in fluid from one compartment to another, an accumulation of fluid, or a depletion of fluid. An event used to initiate impedance signal monitoring may alternatively be an event that is considered evidence of a possible change in fluid status, such as a heart rate or blood pressure change. Perturbations of the patient's fluid status may be provided intentionally to enable observation of the patient response through impedance signal monitoring. An example of an intentional perturbation of the patient's fluid status is an acute programmed high rate pacing interval, a transient programmed therapy intervention, or a change in a therapy such as starting, stopping or adjusting a dosage of a diuretic.

Upon detecting a posture change (or other triggering event as discussed above), the thoracic impedance signal and the extra-thoracic impedance signal are recorded at block 406 and 408. The impedance signals may be recorded at regular time intervals or continuously to obtain mean impedance measurements at multiple sampling times over a period of time following the triggering event.

The impedance signals may be recorded for a predetermined interval of time, which may be minutes, hours, one day or longer periods. At the end of a monitoring period, a fluid status measurement is determined from the thoracic and extra-thoracic impedance signals. Any of the parameters discussed above in conjunction with FIG. 3 may be used to determine the fluid status measurement. In one example, the minimum or maximum impedance recorded during the time period are identified for both of the impedance signals at block 410. For example, a time difference occurring between the minimum impedance of each signal during the monitoring time period is measured at block 412. This time difference is the fluid status measurement that is compared to a threshold at block 414.

If the fluid status measurement crosses a threshold as determined at block 416, the impedance signal data is logged to memory and flagged and/or an alert may be generated at block 418. If a threshold crossing is not detected, the impedance signal data may or may not be stored in memory and the process returns to block 404 to monitor for the next triggering event for initiating another period of impedance monitoring. As described in conjunction with FIG. 4, the threshold crossing of an impedance measurement may additionally cause a therapy adjustment as discussed above.

Figure 6:
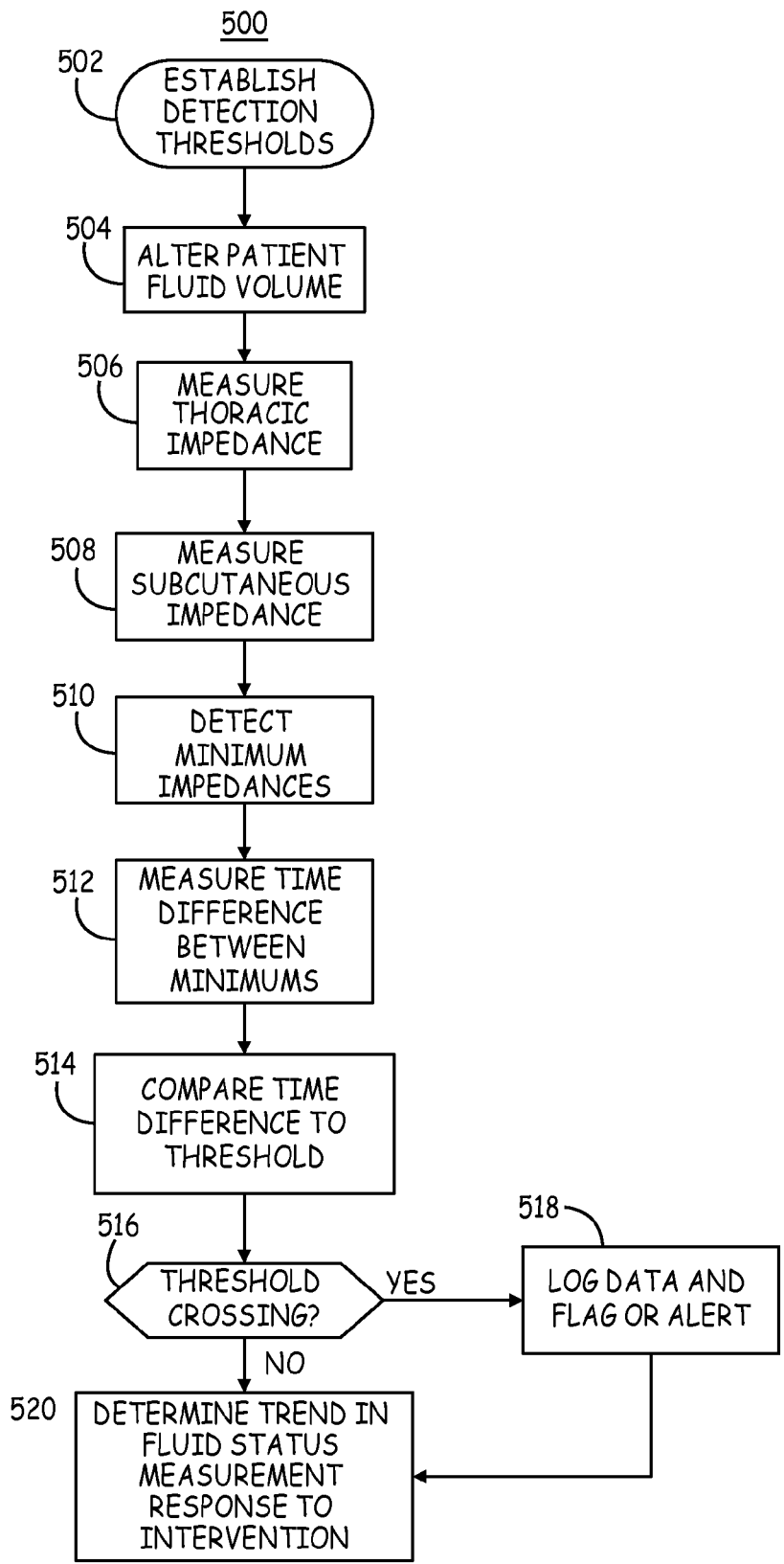
FIG. 6 is a flow chart of a method for monitoring a fluid status of a patient according to yet another embodiment.

FIG. 6 is a flow chart 500 of a method for monitoring a fluid status of a patient according to yet another embodiment. At block 502, thresholds applied to a fluid status measurement are established. At block 504, an intervention is performed to cause an alteration in the patient's fluid volume. This intervention may be performed under direct or indirect clinical supervision and may cause an increase or a decrease in the patient's fluid volume. For example, an infusion of fluid may be administered or a diuretic medication may be withdrawn or decreased, which may cause an increase in fluid volume. Alternatively, fluid may removed through a process such as dialysis or ultrafiltration or by administering or increasing a diuretic medication. In some cases, two or more interventions may be made sequentially to cause an increase then a decrease in fluid volume or vice versa.

The impedance signals are recorded at blocks 506 and 508 and a fluid status measurement is determined from the two impedance signals at block 510 and 512 as described previously. In the example shown, the fluid status measurement is a time difference between minimum impedance measurements, however the fluid status measurement may be any one or combination of measurements described previously herein. The fluid status measurement is compared to a threshold for detecting a fluid status change at block 514 and when a threshold crossing is detected the data may be logged to memory and flagged and/or an alert generated.

As described previously, the threshold crossing may be used in therapy delivery decisions. A therapy may be initiated, stopped, or otherwise adjusted based on the fluid status measurement response to the intervention performed at block 504.

At block 520, a chronic trend in the fluid status measurement response to the intervention performed at block 504 may be determined. For example, the intervention may be performed on a periodic basis to determine if the fluid status measurement changes over time, providing an indication of the overall patient heart failure or renal failure condition, which may include a response to an ongoing therapy. For example, if a heart failure patient is being treated through the use of CRT or a neurostimulation therapy, the patient's response to an intentional perturbation in the fluid volume at block 504 may be checked periodically to determine if the heart failure condition has improved or stabilized and if diuretic medication can be reduced or withdrawn.

Figure 7:
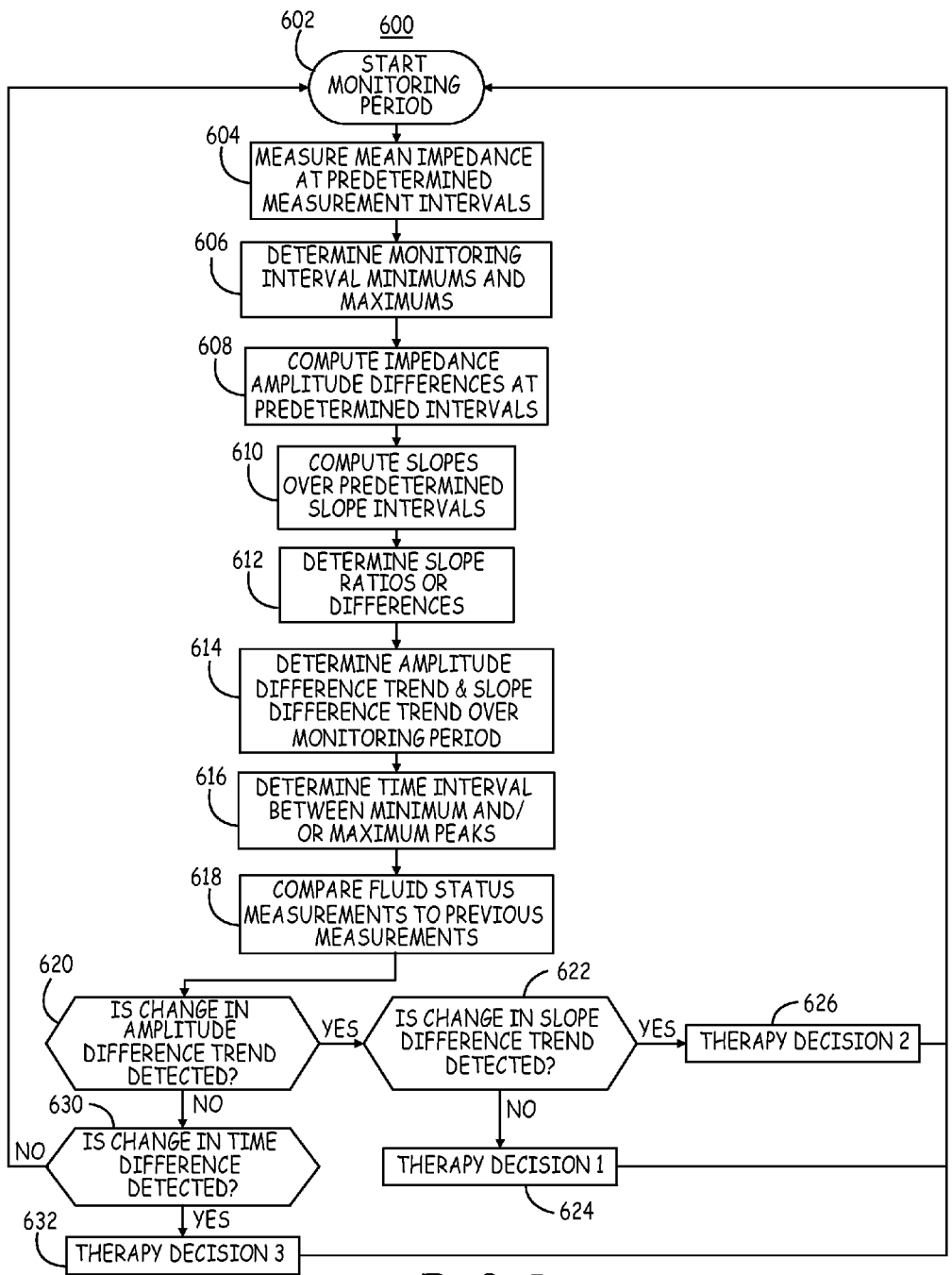
FIG. 7 is a flow chart of a method for monitoring fluid status measurements for use in therapy decision algorithms according to an illustrative embodiment.

FIG. 7 is a flow chart 600 of a method for monitoring fluid status measurements for use in therapy decision algorithms according to an illustrative embodiment. At block 602, a monitoring interval is started. The monitoring interval may be any interval of time, e.g. one hour, one day, one week, one month, etc. The monitoring interval may be performed on a regular repeating basis or be triggered upon detecting a patient condition using another sensor signal, such as a posture change, or upon initiating an intervention that causes a fluid change as described previously. A thoracic and an extra-thoracic impedance signal are recorded when the monitoring interval begins. The thoracic impedance and the extra-thoracic impedance are measured at predetermined measurement intervals throughout the monitoring period at block 604. These measurements may be mean impedance measurements determined from the recorded impedance signal sampled over one or more cardiac cycles or another predetermined sampling interval.

At block 606, a peak thoracic and a peak extra-thoracic impedance measurement are determined for the entire monitoring period. The peak measurements may be maximums, minimums or both.

Amplitude differences between the two impedance signals are computed at predetermined intervals throughout the monitoring period at block 608. In other words, at regular predetermined intervals of time, e.g. every hour over a 24-hour monitoring period, a mean impedance amplitude is determined for both signals and the difference between the thoracic and extra-thoracic mean impedance amplitude is determined.

At block 610, the slope of each of the two impedance signals is determined over a predetermined slope measurement interval. The slope measurement interval may be one minute, several minutes, one hour, several hours, one day or other interval. The slopes may be determined, for example, over a slope measurement interval each time the mean amplitudes are determined. Alternatively, the slopes may be determined at predetermined intervals subsequent to detecting peak measurements of the impedance signals. The predetermined intervals at which slopes are measured may not be equal. For example, slopes may be measured at 5 minute intervals for one hour after detecting a minimum or maximum impedance peak, then at 30 minute intervals, then at one hour intervals over a 24-hour monitoring period. Other slope measurement schedules may be defined in accordance with the monitoring application. At block 612, the ratio or difference between impedance signal slope measurements is determined for each slope measurement interval.

In addition to defining a regular or varying slope measurement schedule, the slope measurement interval itself may be fixed or may vary. For example, initially a slope may be measured over a five minute interval every 30 minutes for the first four hours after detecting a minimum peak then measured over a one hour interval every 4 hours for the remainder of the monitoring period. It is recognized that numerous variations may be conceived for measuring impedance signal amplitudes and slopes and such schedules will be determined in accordance with the patient condition being monitored, therapy being managed, detected events or interventions being performed which initiate a monitoring period, and the corresponding expected impedance signal behavior.

It is further recognized, that predefined measurement schedules and measurement intervals may be established for different monitoring periods and for different events that initiate a monitoring period. For example, a default monitoring period may be a 24-hour monitoring period that is performed repeatedly based on clock time. A triggered monitoring period of a different duration may be initiated during the 24-hour monitoring period in response to a triggering event that is defined by a different monitoring period (shorter or longer than the default period) and with different measurement schedules and measurement intervals. To illustrate, a 24-hour monitoring period may be ongoing, however, detection of a high heart rate during resting activity level may cause an increased frequency of impedance measurements for a 6 hour monitoring period or until the heart rate returns to an expected resting rate. The 24-hour monitoring period may be temporarily interrupted or both monitoring schedules may be performed concurrently. As such, multiple monitoring periods, associated starting events, and measurement schedules and measurement intervals may be defined and may operate singly or concurrently.

At block 614, the trend of the amplitude ratios or differences and the trend of the slope ratios or differences over the monitoring period are determined. The trends may be determined using curve fitting methods, stored as data points defining a curve, or classified generally as increasing, decreasing, variable, etc. These amplitude and slope trends over a monitoring period or portion thereof will be used to detect changes in the impedance response over time due to a change in patient condition or therapeutic intervention. A time difference between a peak impedance (minimum or maximum or both) during the monitoring period is determined at block 616.

Using these fluid status measurements obtained over the current monitoring interval, changes in the impedance behavior can be detected by comparing to previously measured fluid status measurements at block 618. The results of these comparisons can be used in therapy control decision algorithms. For example, at block 620, the trend of the amplitude differences over the monitoring period is compared to the trend of the amplitude differences measured during one or more previous monitoring periods. If the trend of amplitude differences over the monitoring period presents a change compared to previously measured trend(s), the slope trend may be examined at block 622. If the slope trend has not changed, indicating a general shift in one impedance signal relative to the other but not a change in the shape of an impedance signal, the process advances to therapy decision 1 at block 624.

At therapy decision 1, additional analysis of the amplitude difference may be determined. For example, if the difference or ratio indicates decreasing thoracic impedance relative to extra-thoracic impedance, a therapy to address pulmonary edema may be adjusted. If the difference or ratio indicates decreasing extra-thoracic impedance relative to thoracic impedance, a therapy to improve tissue fluid removal may be adjusted. In one example, a drug or neurostimulation therapy to cause vasodilation may be provided.

If a change in the slope difference trend is detected at block 622, the process advances to therapy decision 2 block 626. At this therapy decision, a therapy that addresses a change in the thoracic or extra-thoracic impedance response. In some cases, the slopes may become more disparate indicating a worsening physiological response resulting in greater pulmonary congestion or tissue congestion. A therapy to address heart failure, renal failure, and/or fluid retention may be initiated or increased. In other cases, the slopes may become more similar, indicating an improving physiological response and balance in body fluid removal and retention. A therapy may be reduced or maintained at a current level.

If a change in the amplitude difference trend is not detected at block 620, a detected change in the measured time interval difference between peaks compared to previously measured time interval difference(s) may result in therapy decision 3 at block 632. An increase in the time interval difference may result in an increase in a vasodilator therapy. A decrease in the time interval difference may result in a decrease in a vasodilator therapy.

It is contemplated that the therapy decision blocks 624, 626, and 632 may be performed using input from an analysis of one or more fluid status measurements in any combination. Therapy decision blocks 624, 626, and 632 may be performed for controlling one or more therapies delivered automatically by a device, prescribed by a clinician after receiving a fluid status report or alert, or a combination thereof. While particular examples are provided herein for making therapy delivery decisions based on fluid status measurements determined using at least two impedance measurements, it is recognized that other embodiments for controlling other therapies may be implemented using the methods disclosed herein without departing from the scope of the present disclosure and claims set forth below.

Thus, a medical device system and associated methods for monitoring a patient's fluid status using at least two impedance signals have been presented in the foregoing description with reference to specific embodiments. It is appreciated that various modifications to the referenced embodiments may be made without departing from the scope of the disclosure as set forth in the following claims.

The invention claimed is:

1. A medical device for delivering a cardiac therapy, comprising:
 a plurality of electrodes to sense a first impedance signal along a thoracic electrode vector extending within a portion of a thoracic cavity and a second impedance signal along an extra-thoracic electrode vector extending outside the thoracic cavity;
 a therapy delivery module to deliver the therapy via electrodes of the plurality of electrodes: and
 a processor configured to compare first amplitude measurements corresponding to the first impedance signals and second amplitude measurements corresponding to the second impedance signals, compare first slope measurements corresponding to the first impedance signals and second slope measurements corresponding to the second impedance signals, and control the therapy delivery module to deliver the cardiac therapy in response to the comparing, wherein the processor is further configured to determine amplitude differences between the first amplitude measurements and the second amplitude measurements at a predetermined amplitude difference interval, determine whether the amplitude differences correspond to decreasing impedance along the thoracic electrode vector relative to the extra-thoracic electrode vector, and deliver a first therapy in response to decreasing impedance along the thoracic electrode vector relative to the extra-thoracic electrode vector, and wherein the processor is further configured to determine whether the amplitude differences correspond to decreasing impedance along the extra-thoracic electrode vector relative to the thoracic electrode vector, and deliver a second therapy different from the first therapy in response to decreasing impedance along the extra-thoracic electrode vector relative to the thoracic electrode vector.

2. The medical device of claim 1, wherein the first therapy corresponds to pulmonary edema and the second therapy corresponds to tissue fluid removal.

3. A medical device for delivering a cardiac therapy, comprising:
 a plurality of electrodes to sense a first impedance signal along a thoracic electrode vector extending within a portion of a thoracic cavity and a second impedance signal along an extra-thoracic electrode vector extending outside the thoracic cavity;
 a therapy delivery module to deliver the therapy via electrodes of the plurality of electrodes: and
 a processor configured to compare first amplitude measurements corresponding to the first impedance signals and second amplitude measurements corresponding to the second impedance signals, compare first slope measurements corresponding to the first impedance signals and second slope measurements corresponding to the second impedance signals, and control the therapy delivery module to deliver the cardiac therapy in response to the comparing, wherein the processor is further configured to determine amplitude differences between the first amplitude measurements and the second amplitude measurements, determine an amplitude difference trend in response to the determined amplitude differences, determine slope differences between the first slope measurements and the second slope measurements, determine a slope difference trend in response to the determined slope differences, and determine delivery of the cardiac therapy in response to the amplitude difference trend and the slope difference trend, compare a current determined amplitude difference trend and a previously determined amplitude difference trend, determine amplitude difference trend change in response to the comparing of the current determined amplitude difference trend and a previously determined amplitude difference trend, and determine delivery of the cardiac therapy in response to the determined amplitude difference trend change, and compare a current determined slope difference trend and a previously determined slope difference trend, determine slope difference trend change in response to the comparing of the current determined slope difference trend and a previously determined slope difference trend, and determine delivery of the cardiac therapy in response to the determined slope difference trend change, wherein the processor is further configured to determine whether the amplitude difference indicates either a decreasing impedance along the thoracic electrode vector relative to the extra-thoracic electrode vector or a decreasing impedance along the extra-thoracic electrode vector relative to the thoracic electrode vector, deliver a first therapy in response to decreasing impedance along the thoracic electrode vector relative to the extra-thoracic electrode vector, and deliver a second therapy different from the first therapy in response to decreasing impedance along the extra-thoracic electrode vector relative to the thoracic electrode vector.

4. The medical device of claim 3, wherein the first therapy corresponds to pulmonary edema and the second therapy corresponds to tissue fluid removal.

5. A medical device for delivering a cardiac therapy, comprising:
 a plurality of electrodes to sense a first impedance signal along a thoracic electrode vector extending within a portion of a thoracic cavity and a second impedance signal along an extra-thoracic electrode vector extending outside the thoracic cavity;
 a therapy delivery module to deliver the therapy via electrodes of the plurality of electrodes: and
 a processor configured to compare first amplitude measurements corresponding to the first impedance signals and second amplitude measurements corresponding to the second impedance signals, compare first slope measurements corresponding to the first impedance signals and second slope measurements corresponding to the second impedance signals, and control the therapy delivery module to deliver the cardiac therapy in response to the comparing, wherein the processor is further configured to determine amplitude differences between the first amplitude measurements and the second amplitude measurements, determine an amplitude difference trend in response to the determined amplitude differences, determine slope differences between the first slope measurements and the second slope measurements, determine a slope difference trend in response to the determined slope differences, and determine delivery of the cardiac therapy in response to the amplitude difference trend and the slope difference trend, and wherein the processor is further configured to compare a current determined amplitude difference trend and a previously determined amplitude difference trend, determine whether there is a change in amplitude difference trend in response to the comparing of the current determined amplitude difference trend and a previously determined amplitude difference trend, and deliver a first therapy in response to determining no change in amplitude difference trend.

6. The medical device of claim 5, wherein the processor is further configured to compare a current determined slope difference trend and a previously determined slope difference trend in response to determining change in amplitude difference trend, determine whether there is a change in slope difference trend in response to the comparing of the current determined slope difference trend and a previously determined slope difference trend, deliver a second therapy in response to determining no change in slope difference trend, and deliver a third therapy in response to determining change in slope difference trend.

7. A method for determining delivery of a cardiac therapy, comprising:
 determining a first impedance signal along a thoracic electrode vector extending within a portion of a thoracic cavity;
 determining a second impedance signal along an extra-thoracic electrode vector extending outside the thoracic cavity;
 comparing first amplitude measurements corresponding to the first impedance signals and second amplitude measurements corresponding to the second impedance signals;
 comparing first slope measurements corresponding to the first impedance signals and second slope measurements corresponding to the second impedance signals;
 determining delivery of the cardiac therapy in response to the comparing determining amplitude differences between the first amplitude measurements and the second amplitude measurements at a predetermined amplitude difference interval;

determining whether the amplitude differences correspond to decreasing impedance along the thoracic electrode vector relative to the extra-thoracic electrode vector;

delivering a first therapy in response to decreasing impedance along the thoracic electrode vector relative to the extra-thoracic electrode vector;

determining whether the amplitude differences correspond to decreasing impedance along the extra-thoracic electrode vector relative to the thoracic electrode vector; and delivering a second therapy different from the first therapy in response to decreasing impedance along the extra-thoracic electrode vector relative to the thoracic electrode vector.

8. The method of claim 7, wherein the first therapy corresponds to pulmonary edema and the second therapy corresponds to tissue fluid removal.

9. A method for determining delivery of a cardiac therapy, comprising:

determining a first impedance signal along a thoracic electrode vector extending within a portion of a thoracic cavity;

determining a second impedance signal along an extra-thoracic electrode vector extending outside the thoracic cavity;

comparing first amplitude measurements corresponding to the first impedance signals and second amplitude measurements corresponding to the second impedance signals;

comparing first slope measurements corresponding to the first impedance signals and second slope measurements corresponding to the second impedance signals;

determining delivery of the cardiac therapy in response to the comparing;

determining amplitude differences between the first amplitude measurements and the second amplitude measurements;

determining an amplitude difference trend in response to the determined amplitude differences;

determining slope differences between the first slope measurements and the second slope measurements;

determining a slope difference trend in response to the determined slope differences; and determining delivery of the cardiac therapy in response to the amplitude difference trend and the slope difference trend;

comparing a current determined amplitude difference trend and a previously determined amplitude difference trend;

determining amplitude difference trend change in response to the comparing of the current determined amplitude difference trend and a previously determined amplitude difference trend;

determining delivery of the cardiac therapy in response to the determined amplitude difference trend change;

comparing a current determined slope difference trend and a previously determined slope difference trend;

determining slope difference trend change in response to the comparing of the current determined slope difference trend and a previously determined slope difference trend;

determining delivery of the cardiac therapy in response to the determined slope difference trend change;

determining whether the amplitude difference indicates either a decreasing impedance along the thoracic electrode vector relative to the extra-thoracic electrode vector or a decreasing impedance along the extra-thoracic electrode vector relative to the thoracic electrode vector;

delivering a first therapy in response to decreasing impedance along the thoracic electrode vector relative to the extra-thoracic electrode vector; and delivering a second therapy different from the first therapy in response to decreasing impedance along the extra-thoracic electrode vector relative to the thoracic electrode vector.

10. The method of claim 9, wherein the first therapy corresponds to pulmonary edema and the second therapy corresponds to tissue fluid removal.

11. A method for determining delivery of a cardiac therapy, comprising:

determining a first impedance signal along a thoracic electrode vector extending within a portion of a thoracic cavity;

determining a second impedance signal along an extra-thoracic electrode vector extending outside the thoracic cavity;

comparing first amplitude measurements corresponding to the first impedance signals and second amplitude measurements corresponding to the second impedance signals;

comparing first slope measurements corresponding to the first impedance signals and second slope measurements corresponding to the second impedance signals;

determining delivery of the cardiac therapy in response to the comparing;

determining amplitude differences between the first amplitude measurements and the second amplitude measurements;

determining an amplitude difference trend in response to the determined amplitude differences;

determining slope differences between the first slope measurements and the second slope measurements;

determining a slope difference trend in response to the determined slope differences;

determining delivery of the cardiac therapy in response to the amplitude difference trend and the slope difference trend;

comparing a current determined amplitude difference trend and a previously determined amplitude difference trend;

determining whether there is a change in amplitude difference trend in response to the comparing of the current determined amplitude difference trend and a previously determined amplitude difference trend; and delivering a first therapy in response to determining no change in amplitude difference trend.

12. The method of claim 11, further comprising:

comparing a current determined slope difference trend and a previously determined slope difference trend in response to determining change in amplitude difference trend;

determining whether there is a change in slope difference trend in response to the comparing of the current determined slope difference trend and a previously determined slope difference trend;

delivering a second therapy in response to determining no change in slope difference trend; and delivering a third therapy in response to determining change in slope difference trend.

* * * * *